United States Patent
Migachyov

[11] Patent Number: 5,989,179
[45] Date of Patent: Nov. 23, 1999

[54] BLADDER CONTROL DEVICE HOUSING AND METHOD

[75] Inventor: Valery Migachyov, San Antonio, Tex.

[73] Assignee: HK Medical Technologies Incorporated, San Antonio, Tex.

[21] Appl. No.: 08/888,993

[22] Filed: Jul. 7, 1997

[51] Int. Cl.⁶ .................................................... A61F 2/00
[52] U.S. Cl. ................................................ 600/29; 600/31
[58] Field of Search ................. 600/29–31; 128/DIG. 25

[56] References Cited

U.S. PATENT DOCUMENTS

| | | |
|---|---|---|
| 3,628,530 | 12/1971 | Schwartz . |
| 3,812,841 | 5/1974 | Isaacson . |
| 4,246,896 | 1/1981 | Horne, Jr. et al. . |
| 4,553,533 | 11/1985 | Leighton . |
| 4,679,546 | 7/1987 | van Waalwijk van Doorn et al. . |
| 4,969,474 | 11/1990 | Schwarz ................................. 128/885 |
| 5,041,092 | 8/1991 | Barwick ................................. 604/104 |
| 5,123,428 | 6/1992 | Schwarz ................................. 128/885 |
| 5,140,999 | 8/1992 | Ardito ..................................... 128/885 |
| 5,437,604 | 8/1995 | Kulisz et al. ............................. 600/30 |
| 5,662,582 | 9/1997 | Levius et al. ............................ 600/29 |
| 5,704,353 | 1/1998 | Kalb et al. ............................... 600/29 |

FOREIGN PATENT DOCUMENTS

WO 96/18431   6/1996   WIPO .

*Primary Examiner*—Linda C. M. Dvorak
*Assistant Examiner*—Rosiland Kearney
*Attorney, Agent, or Firm*—Crompton, Seager & Tufte

[57] ABSTRACT

An intraurethral female bladder control apparatus and method for nonsurgically inserting the apparatus distally into a patient. A preferred apparatus has a rigid plastic inner housing with soft, flexible retainer attached distally and a flow control unit mounted within the inner housing lumen. A rigid, plastic outer housing having a softer proximal retainer and distal, upper tip, surrounds the inner housing and has the distal retainer within prior to insertion. In use, the upper tip is inserted through the urethra into the bladder and the inner housing advanced to deploy the distal retainer within the bladder floor.

12 Claims, 9 Drawing Sheets

BLADDER CONTROL DEVICE HOUSING AND METHOD

RELATED APPLICATIONS

The present invention is related to U.S. application Ser. No. 08/515,920 filed on Aug. 16, 1995, entitled INTRAURETHRAL BLADDER CONTROL DEVICE WITH RETAINER APPARATUS and U.S. application Ser. No. 08/515,564 filed on Aug. 16, 1995, entitled BLADDER CONTROL INSERTION APPARATUS AND METHOD.

FIELD OF THE INVENTION

The invention relates generally to artificial female bladder control valves. More specifically, the invention relates to an intra-urethral bladder flow control device and method for inserting same.

BACKGROUND OF THE INVENTION

Urinary incontinence, in both males and females, is a significant medical problem. The use of bladder control devices, sometimes referred to as artificial sphincters or prosthetic urethral valves, is well known. Bladder control devices may be required due to loss of control or removal of the urinary sphincter muscle. The use of such intraurethral valve apparatus and general knowledge in the field of art can be evidenced by, for example, U.S. Pat. Nos. 4,553,533; 4,679,546; 4,969,474; 5,123,428 and 5,140,999. One goal in the design of such devices is the safe and secure retention of the bladder control or valve device in the female urethra. It is desirable to have the placement of the bladder control apparatus in the urethra performed easily and nonsurgically. It is important not only that the device be securely retained once placed in the urethra, but also that a simple, nonsurgical means of removing the device be present. Optimally, when required, the device could be removed by grasping an exposed part and pulling. A device should have both soft, more pliable surfaces for retaining the device and harder, more rigid components providing the strength required for insertion and removal. A device would optimally include strong materials for the valve portion and also be formed of non-metallic materials where exposed to the body. Various prior art devices have not met all of these criteria.

SUMMARY OF THE INVENTION

The present invention includes a female bladder control apparatus and method for placement of the apparatus. The invention includes a housing having a lumen therethrough and a flow control unit disposed within, a distal retainer attached to the housing distal region, and a proximal retainer attached to the housing proximal region. The distal retainer is adapted to be received within the housing lumen and is biased to expand radially when pushed distally from the housing lumen. The distal retainer can include radial arms and interconnecting rim. The distal end is to be positioned near the bladder floor, and the proximal end is to be positioned near the urethral meatus.

The device housing preferably includes an inner housing subassembly and an outer housing subassembly. The inner housing subassembly can have the distal retainer attached thereto and the flow control unit contained within. The outer housing subassembly can have the proximal retainer attached proximally and a soft, internally expandable elastic upper tip attached distally. The housing can be formed of harder, more rigid plastic, while the retainers and tip can be formed of softer, medical grade silicone or polypropilene rubber.

The inner housing subassembly can have a proximal region adapted to be releasably attached with threads, to a stainless steel insertion rod. The outer housing subassembly can have a proximal region adapted to be releasably attached to a pusher assembly having a quarter turn locking ring. The pusher assembly preferably includes a distal barrel and proximal plunger, for containing and pushing the insertion rod and inner housing subassembly distally.

In use, the distal retainer can be folded and retracted within the outer housing upper tip. The housing upper tip can be lubricated and advanced distally through the urethra. With tip advanced, the inner housing subassembly can be advanced distally, forcing the distal retainer out of the upper tip. The inner housing subassembly can be advanced by providing an insertion rod and releasably securing the insertion rod to the inner housing subassembly proximal end. The insertion rod can be more easily advanced by providing a pusher assembly, releasably attaching it to the outer housing subassembly proximal end with a locking ring, and using it to advance the insertion rod and attached inner housing subassembly, thereby advancing and deploying the distal retainer within the bladder.

DETAILED DESCRIPTION OF THE PREFERRED EMBODIMENTS

Figure 1:
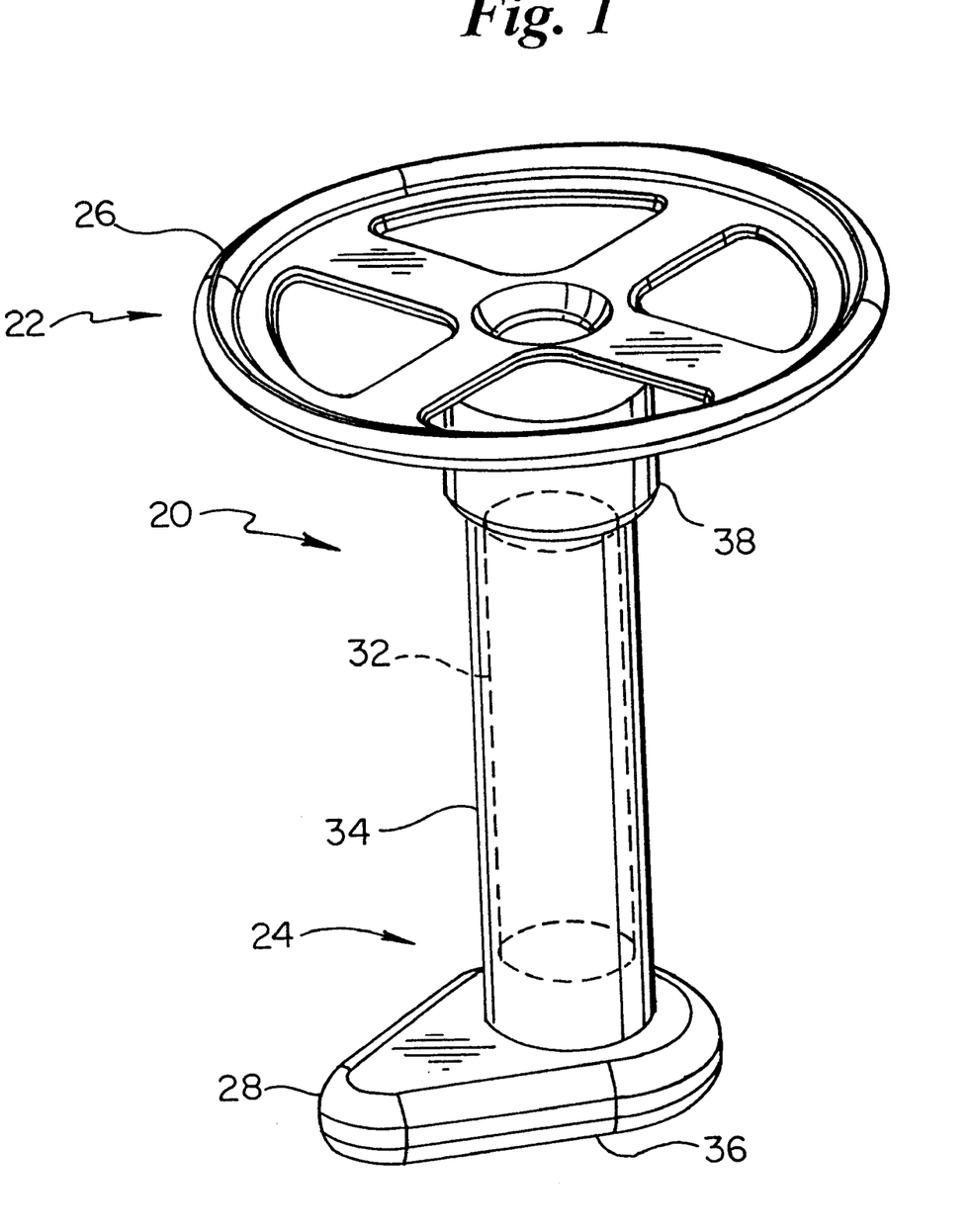
FIG. 1 is a perspective view of a bladder control device according to the present invention, including inner and outer housing subassemblies, with distal retainer expanded.

FIG. 1 illustrates an assembled bladder control device 20 having an inner housing subassembly 22 and an outer housing subassembly 24. Bladder control device 20 includes a distal portion 26 for insertion within the bladder and a proximal portion 28 which will extend from the urethra once in place within a patient. Inner housing subassembly 22 includes a distal retainer 30 attached to the distal portion of an inner tube 33 (shown in FIG. 2), where the inner tube includes a flow control unit 32, shown in phantom. Outer housing subassembly 24 includes an outer tube 34, a proximal retainer 36, and an upper tip 38, shown expanded about the inner tube.

Figure 2:
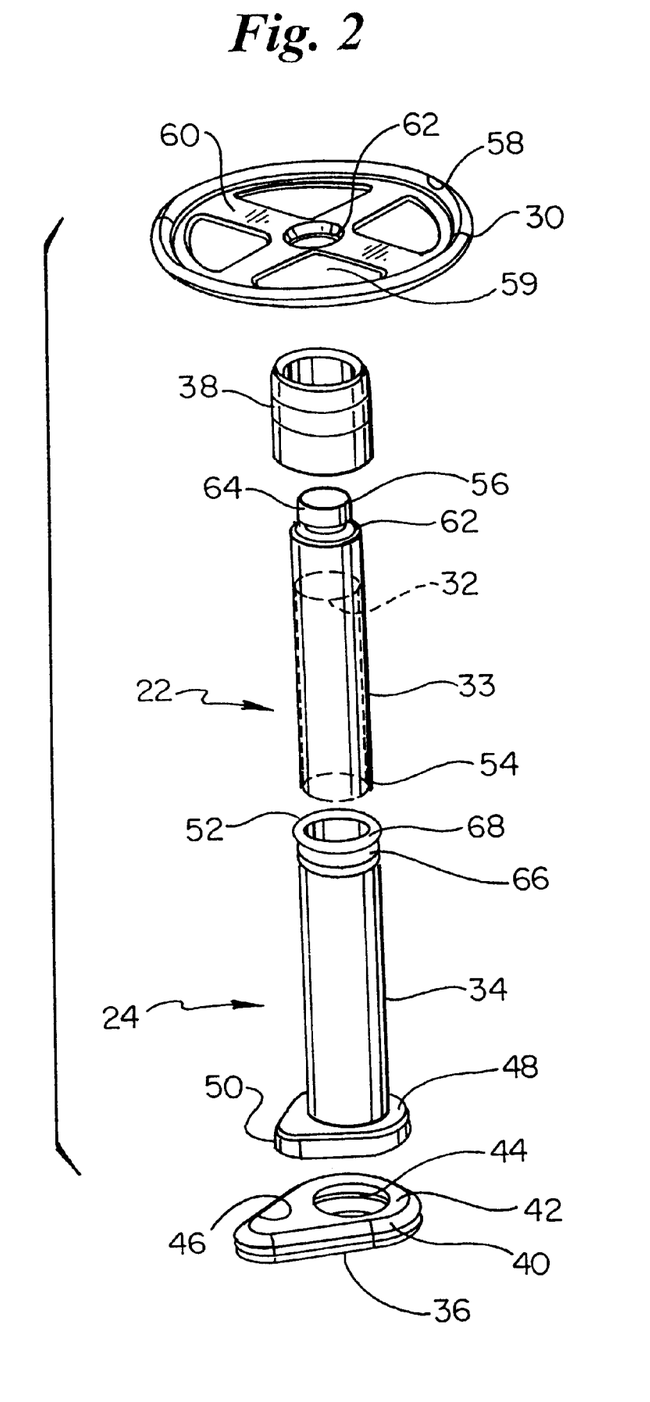
FIG. 2 is an exploded, perspective view of the device of FIG. 1.

Referring now to FIG. 2, bladder control device 20 is illustrated in exploded form. Inner housing subassembly 22 extends from a proximal region 54 to a distal region 56 and includes distal retainer 30. Inner housing subassembly 22 includes flow control unit 32 which can include a stainless steel housing, stopper, upper ring, lower ring and spring, as disclosed in U.S. application Ser. No. 08/515,920 filed on Aug. 16, 1995, entitled INTRAURETHRAL BLADDER CONTROL DEVICE WITH RETAINER APPARATUS, herein incorporated by reference. Inner tube 33 includes a distal, annular recess 62 and an annular lip 64 adapted for attachment to a hub portion 59 of distal retainer 30. Inner tube 33 and distal retainer hub portion 59 have a lumen therethrough for passage of fluids. The proximal end of inner tube 33 can be adapted to receive and releasably secure the distal end of an insertion rod (not shown in FIG. 2). In a preferred embodiment, the proximal end of inner tube 33 includes a female thread or bayonet fitting to receive and releasably secure the male thread or bayonet fitting of an insertion rod.

Figure 6:
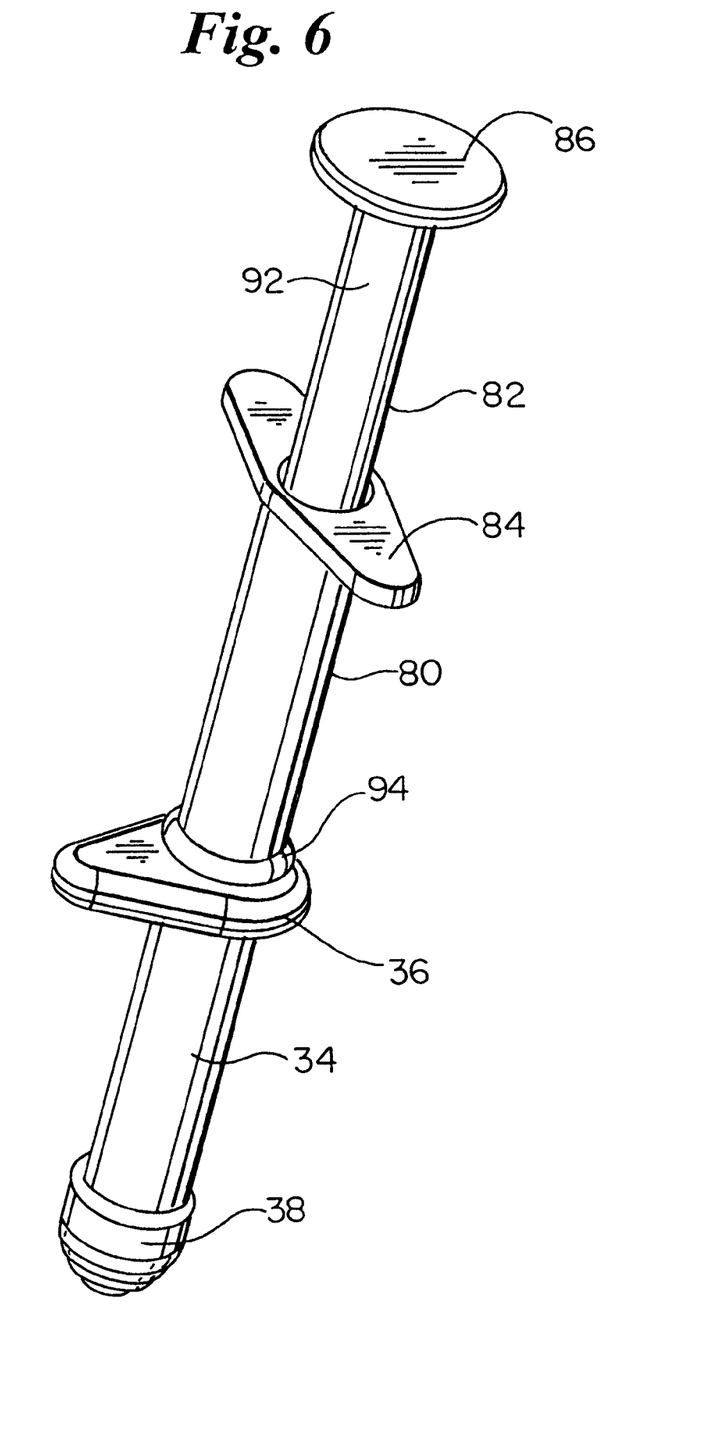
FIG. 6 is a perspective view of the pusher assembly of FIG. 5 attached to the outer housing subassembly of FIG. 3, ready for insertion of the distal retainer of FIG. 1.

Outer housing subassembly 24 extends from a proximal region 50 to a distal region 52 and includes an outer tube 34. Outer tube 34 has a distal annular recess or groove 66 and an annular lip or ring 68 adapted for attachment to upper tip 38. Outer tube 34 is preferably formed from polyethylene, high density polyethylene, or ultra high molecular weight polyethylene. Outer tube 34 has a lumen which is capable of slidably receiving inner tube 33. The proximal portion of outer tube 34 includes an upper plate 48 and contains means for releasably securing the distal end of a pusher assembly, such as a quarter turn locking ring (as shown in FIG. 6). Proximal retainer 36 in a preferred embodiment is formed of a soft, medical grade silicon rubber or polypropylene. Proximal retainer 36 can expand over the proximal portion of the outer tube 34 secured by a soft upper lip 46 with an opening 44. Proximal retainer 36 preferably also has a soft lower lip (not shown in FIG. 2) with an opening adapted to receive the distal end of a pusher assembly (shown in FIG. 6). Proximal retainer 36 can be fixedly attached to the proximal portion of outer tube 34 with adhesive or stretching.

Figure 3:
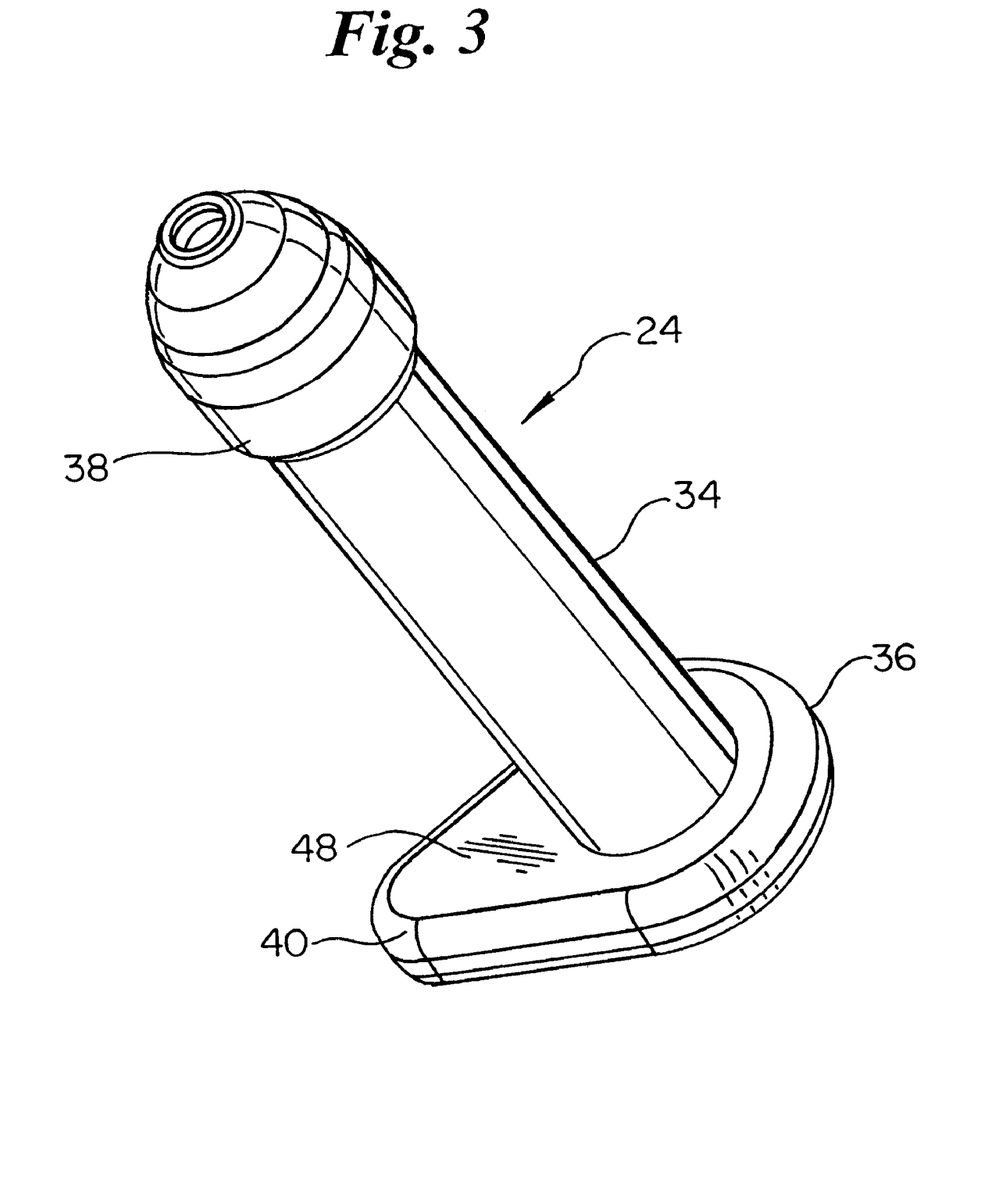
FIG. 3 is a perspective view of the outer housing subassembly of FIG. 1.

Referring now to FIG. 3, outer housing subassembly 24 is shown in perspective, extending from proximal retainer 36, over outer tube 34, to upper tip 38. Upper tip 38 is preferably formed of a soft, elastic material capable of both advancement through the urethra and expansion to contain a retracted distal retainer within. Upper tip 38 is preferably formed of medical grade silicone or polypropilene rubber. Soft skirt portion 40 wraps around plate 48, providing a soft material for contact with the urethral meatus.

Figure 4:
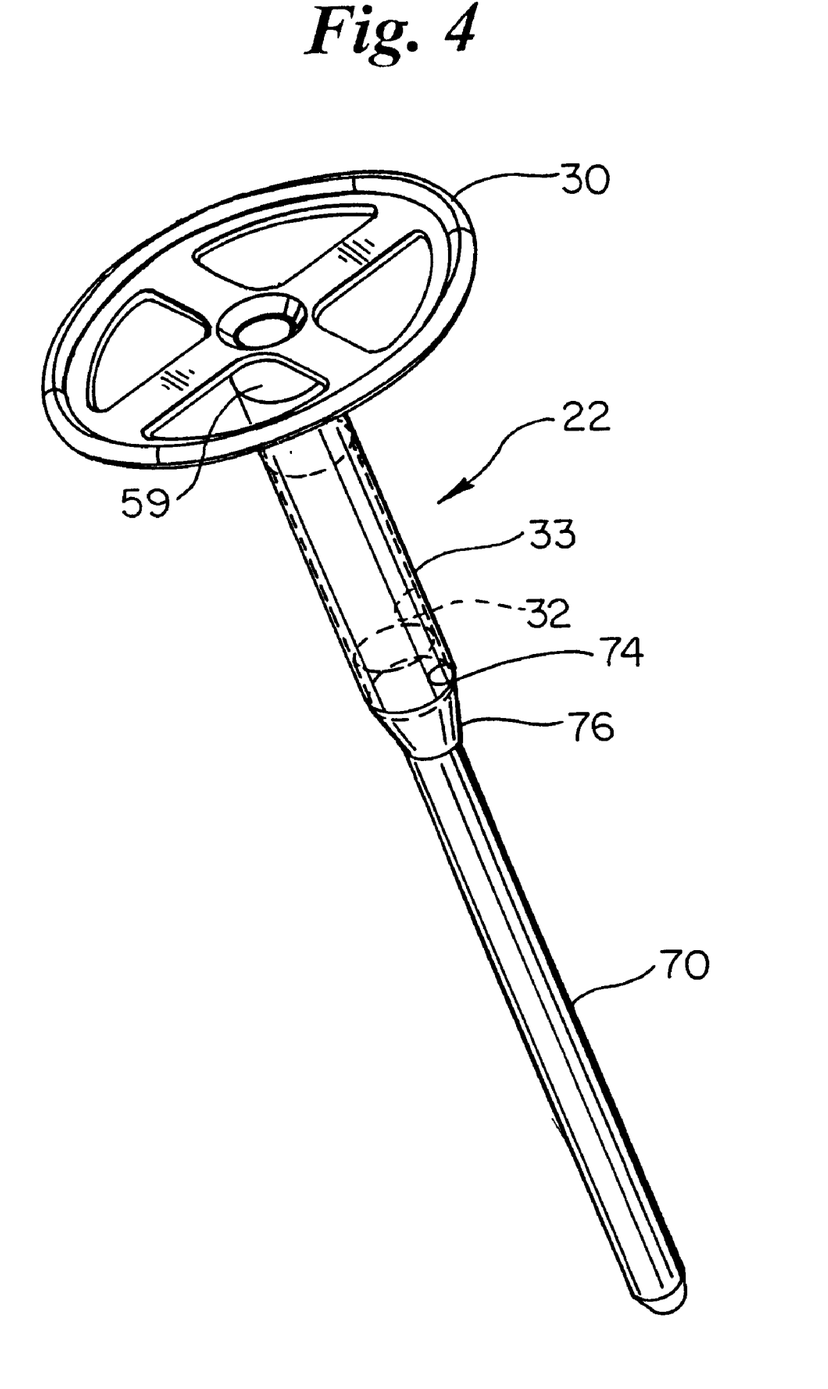
FIG. 4 is a perspective view of a flow control unit insertion subassembly.
Figure 7:
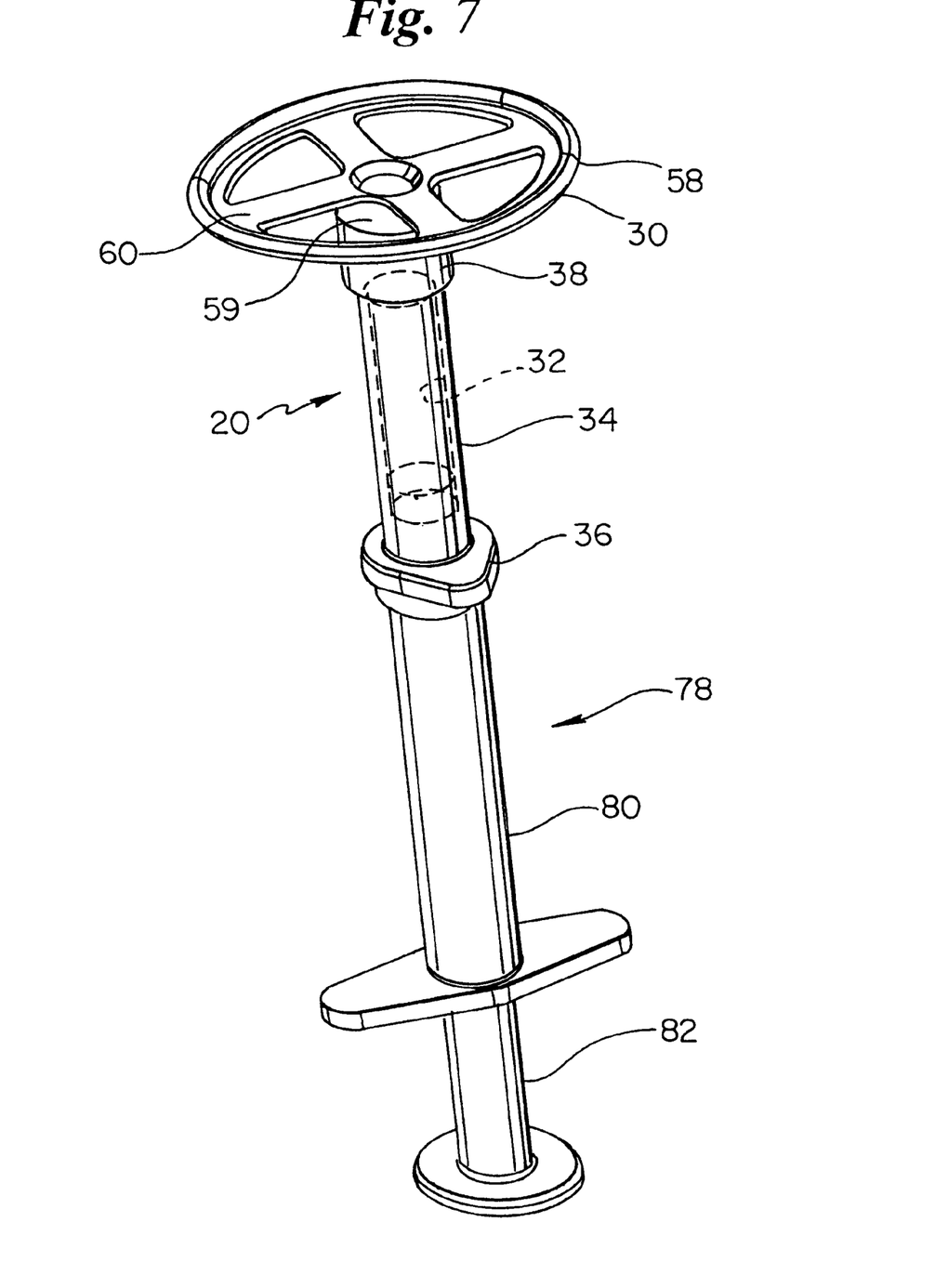
FIG. 7 is a perspective view of the pusher and outer housing subassemblies of FIG. 7 after insertion of the flow control unit and opening of the distal retainer.

Referring now to FIG. 4, inner housing subassembly 22 is illustrated, including inner tube 33 having distal retainer 30 fixedly attached at the distal end. Distal retainer hub portion 59 is preferably integrally formed with distal retainer 30, and is preferably fixedly attached to inner tube 33 with adhesive or stretching. In a preferred embodiment, upper tip 38 of the outer housing subassembly is adapted to receive hub portion 59, with hub portion 59 and upper tip 38 forming a very tight, friction fit (as illustrated in FIG. 7). In another embodiment, upper tip 38 grips the outside of inner tube 33. Inner tube 33 is preferably formed of a strong, rigid plastic material such as polyethylene, high density polyethylene, or ultra high molecular weight polyethylene. Contained within inner tube 33 is flow control unit 32, shown is phantom. In one embodiment, inner tube 33 includes means for releasably securing an outer housing subassembly slid thereover, such as a bayonet fitting or threads. This securing means can supplant the tight friction fit of upper tip 38 gripping distal retainer hub portion 59. Insertion rod 70 includes a distal shoulder 76 adapted to releasably secure the insertion rod to inner tube 33. A preferred embodiment includes a distal, male, threaded portion on insertion rod 70 which extends within a proximal, female threaded portion of inner tube 33, indicated at 74. Insertion rod 70 is preferably formed of stainless steel. Insertion rod 70 is ultimately used to force distal retainer 30 distally out of the outer housing subassembly upper tip and into the bladder, thereby allowing the expansion of the distal retainer.

Figure 5:
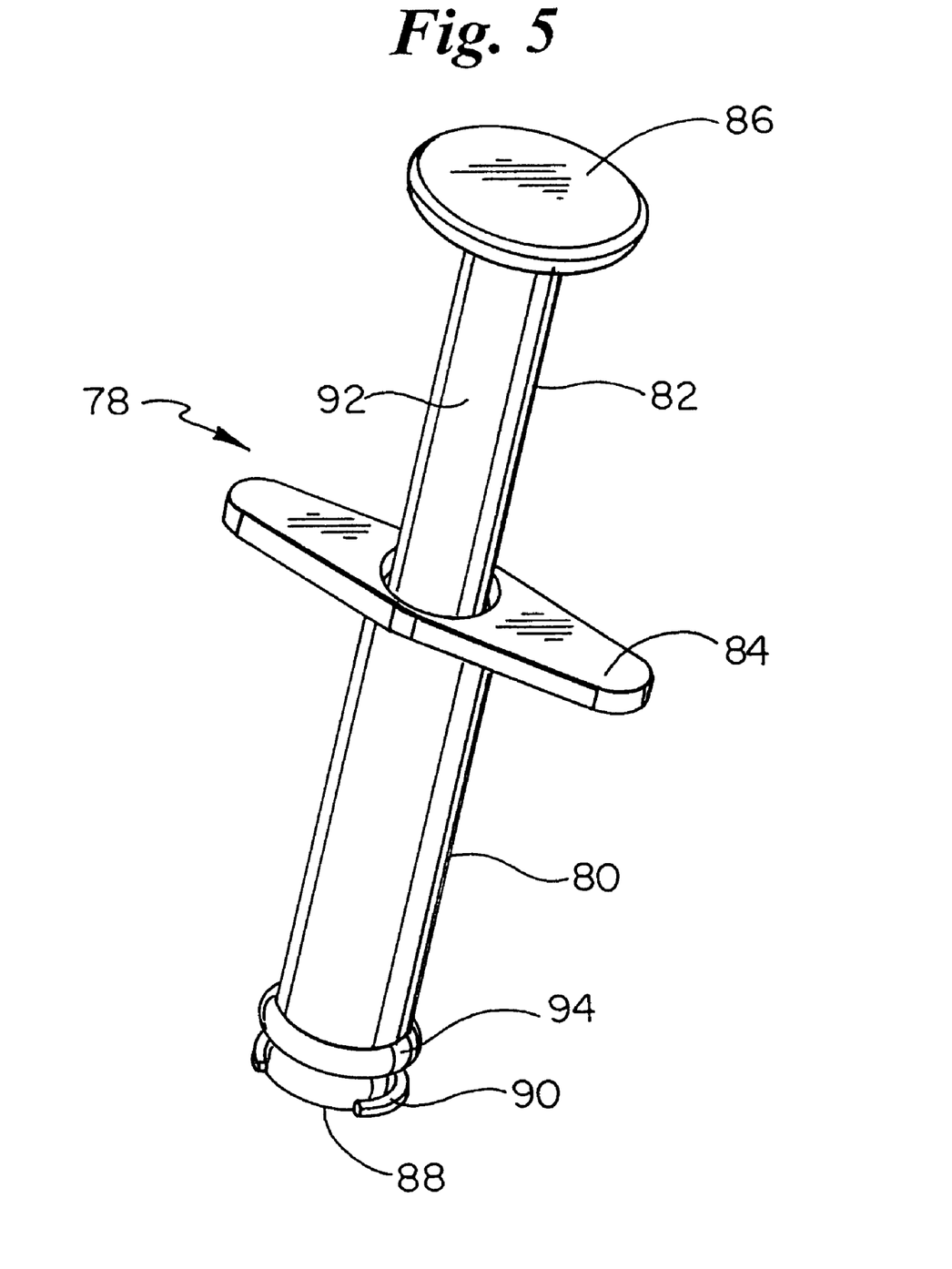
FIG. 5 is a perspective view of a pusher assembly for insertion of the distal retainer of FIG. 1.

Referring now to FIG. 5, a pusher assembly 78 including a barrel 80 and a plunger 82 is illustrated. Barrel 80 and plunger 82 are preferably formed of polyethylene or ABS plastic. Plunger 82 includes a thumb rest 86 and a hollow cylinder 92 capable of slidably receiving the proximal end of the insertion rod. The distal end of barrel 80 has a locking tip 88 including a locking ring 90 and a stop ring 92. Locking tip is adapted to be releasably attached within proximal retainer upper plate 48, in bayonet fashion, as illustrated in FIG. 6. After attachment of locking tip 88 to proximal retainer upper plate 48, force can be applied to finger flanges 84 and thumb rest 86, forcing the contained insertion rod distally into the bladder control device, forcing the inner housing subassembly distally into the patient and contained distal retainer 30 out of upper tip 38.

Referring now to FIG. 7, pusher assembly 78 is illustrated with plunger 82 inserted distally into barrel 80, forcing inner tube 32 within outer tube 34 distally, forcing distal retainer 30 out of upper tip 38. A preferred embodiment distal retainer is formed of an elastic material such a soft medical grade silicone or polypropylene rubber. A preferred retainer has arms 60 which extend radially away from the urethra, and rim 58 interconnect connecting arms 60 circumferentially. Arms 60 expand radially when free of soft upper tip 38 and provide resistance to bladder control device 20 moving proximally out of the patient. Proximal retainer 36 provides resistance to movement distally into the patient, as a portion of proximal retainer 36 is rigid, while distal retainer 30 is flexible in a preferred embodiment.

Figure 8A:
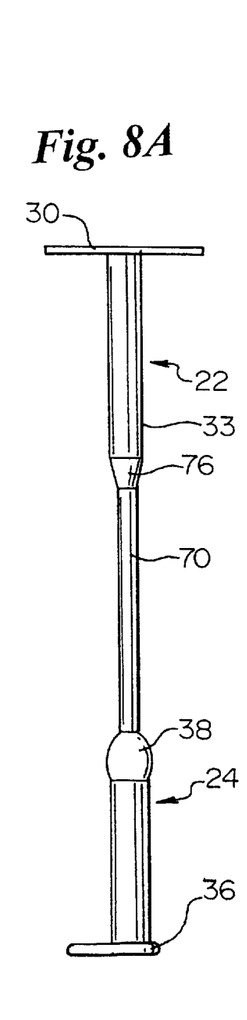
FIG. 8A is a plan view of an inner housing subassembly with distal retainer expanded, having an insertion rod attached proximally and an outer housing subassembly at the insertion rod proximal end.
Figure 8B:
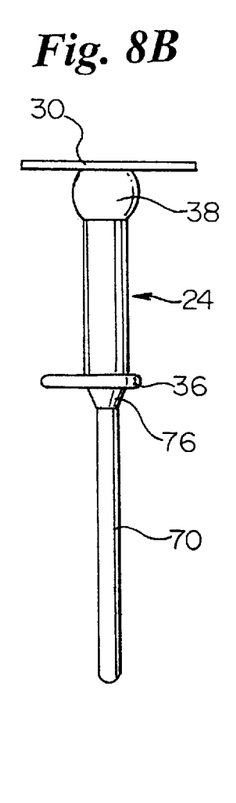
FIG. 8B is a plan view illustrating the outer housing subassembly of FIG. 8A slid distally over the insertion rod to the distal retainer.

Use of an embodiment of the invention is illustrated in FIGS. 8A through 8I. FIG. 8A illustrates inner housing subassembly 22 with distal retainer 30 expanded at the distal end, having a flow control unit within (not illustrated in FIG. 8A) with the distal end of insertion rod 70 releasably secured to the proximal end of inner housing subassembly 22, having shoulder 76 mated to inner tube 33. The proximal end of insertion rod 70 is slidably received within the opening in the distal end of the upper tip 38 of outer housing subassembly 24. In FIG. 8B, outer housing subassembly 24 has been slid distally over insertion rod 70 and inner tube 33, with outer housing soft upper tip 38 making contact with expanded distal retainer 30. In one embodiment, upper tip 38 is formed of an elastomeric material having sufficient strength to grippingly engage inner tube 33 and distal retainer hub portion 59 (not show in FIG. 8B). In a preferred embodiment, the gripping strength of upper tip 38 is sufficiently strong to allow distal retainer 30 to be pulled proximally through the urethra by pulling proximally on outer housing subassembly 24, without allowing outer housing subassembly 24 to separate from inner housing subassembly 22. Another method of removing the bladder control device is to releasably attach insertion rod 20 to inner housing subassembly 24, and pull proximally on insertion rod 20. Insertion rod distal shoulder 76 may be seen protruding proximally from proximal retainer 36. Soft upper tip 38 of outer housing subassembly 24 has expanded in outside diameter as it now contains inner tube 33 within.

Figure 8C:
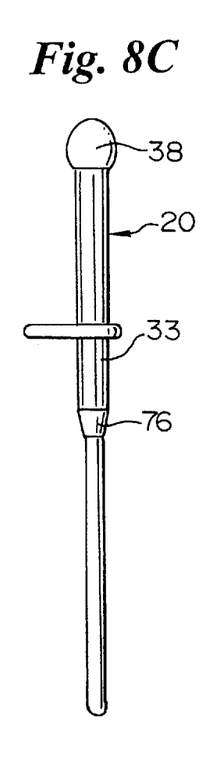
FIG. 8C is a plan view illustrating the outer housing subassembly of FIG. 8C after the insertion rod has been pulled proximally, retracting the distal retainer within the distal tip of the outer housing subassembly.
Figure 8D:
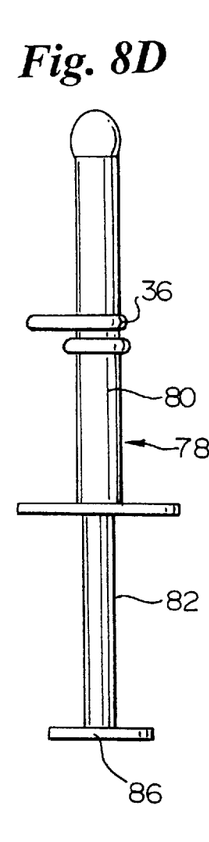
FIG. 8D is a plan view illustrating a bladder control device ready for insertion, having the pusher subassembly inserted over the insertion rod of FIG. 8C and attached to the outer housing subassembly.

In FIG. 8C, by grasping and holding outer tube 34 and pulling insertion rod 70 proximally, flexible distal retainer 30 has been pulled within soft upper housing tip 38. Distal retainer 30 should be lubricated prior to being pulled within upper tip 38. Insertion rod 70 is then retracted proximally further from outer tube 34. In FIG. 8D, pusher assembly 78 has been inserted over insertion rod 70, and releasably secured to the proximal end of outer housing subassembly 24. The proximal end of insertion rod 70 is contained within pusher barrel 80 and plunger 82, with the insertion rod proximal end near plunger thumb rest 86. In the embodiment shown, pusher barrel 80 distally engages proximal retainer 36. Plunger 82 can be retracted proximally. The device is now ready for insertion within the patient.

Figure 8E:
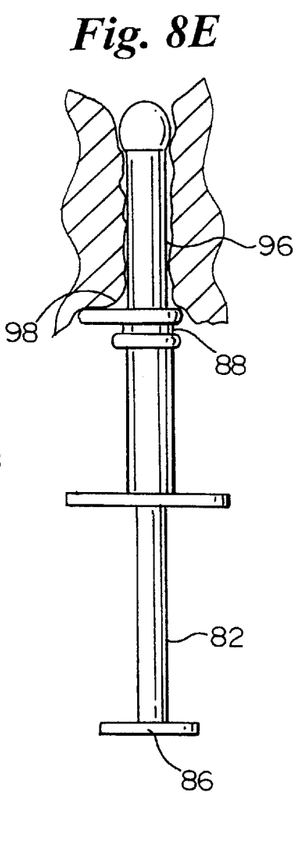
FIG. 8E is a plan view illustrating the pusher and bladder control device of FIG. 8D inserted within a cross section of the female urethra.
Figure 8F:
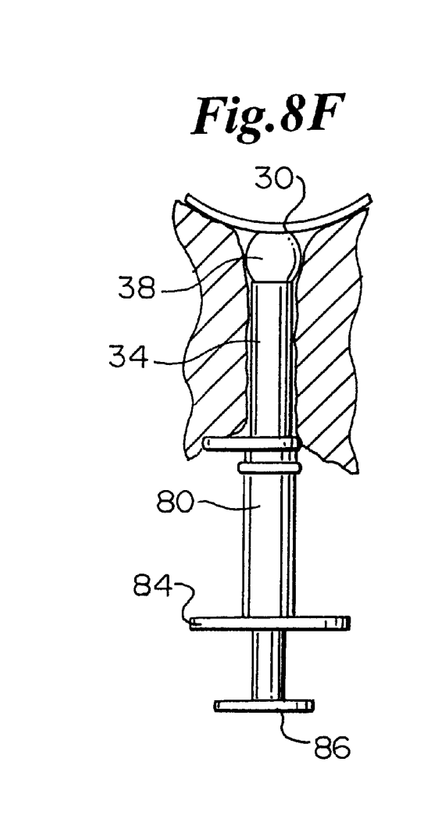
FIG. 8F is a plan view of the bladder control device of FIG. 8E after the plunger has been pushed distally, freeing and expanding the distal retainer into the bladder.

In FIG. 8E, bladder control device 20 has been inserted into the female urethra, such that the proximal retainer is in contact with urethral meatus 98. Plunger 82 remains retracted. In FIG. 8F, plunger thumb rest 86 has been advanced distally toward finger flange 84, with thumb rest 86 pushing against the proximal end of insertion rod 70 contained within plunger 82. Pushing insertion rod 70 and attached inner tube 33 forces distal retainer 30 out of surrounding soft upper tip 38. Distal retainer 30 expands out of upper tip 38, attaining a radial extent greater than the diameter of the urethra opening into the bladder.

Figure 8G:
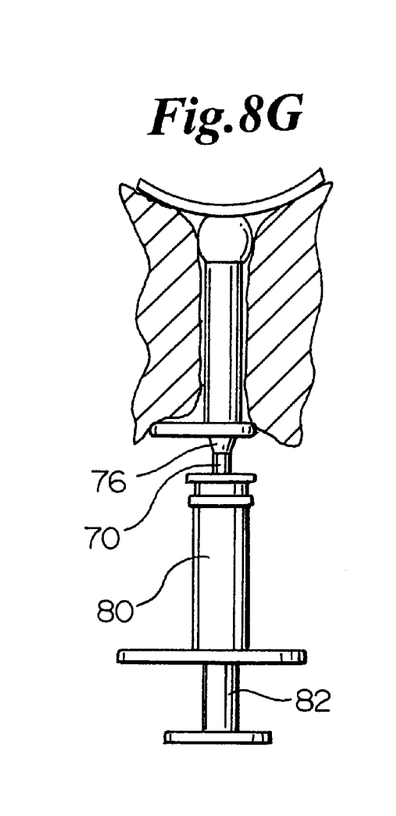
FIG. 8G is a plan view of the bladder control device of FIG. 8F after detaching the pusher assembly from the device.
Figure 8H:
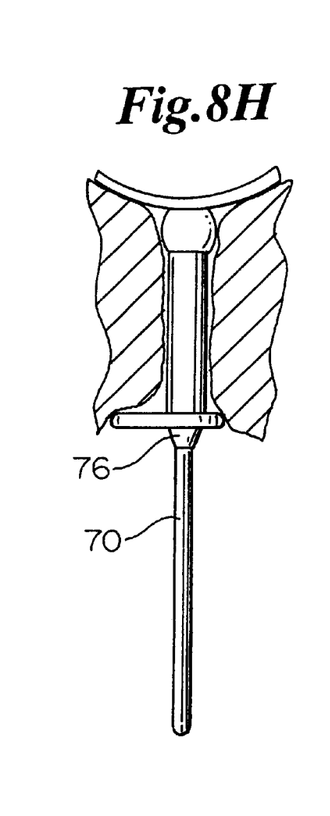
FIG. 8H is a plan view of the bladder control device of FIG. 8G after removing the pusher assembly.
Figure 8I:
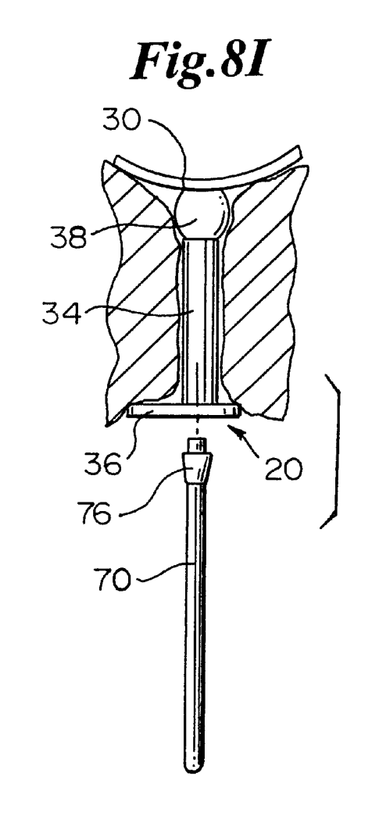
FIG. 8I is a plan view of the bladder control device of FIG. 8G after detaching the insertion rod.

In FIG. 8G, pusher barrel 80 mechanism has been rotated, freeing pusher assembly 78 from bladder control device 20. Pusher assembly 78 has been partially retracted over insertion rod 70. In FIG. 8H, pusher assembly 78 has been fully retracted, exposing the still attached, insertion rod 70. In FIG. 8I, insertion rod 70 has been rotated, freeing it from attachment to inner tube 33. Bladder control device 20 is now in place within the urethra.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A bladder control apparatus for placement in the urethra of a female patient, having a distal end for placement near the bladder and a proximal end for placement near the urethral meatus, comprising:

a housing having a proximal end and a distal end and a lumen extending therethrough such that fluid from the bladder can flow through the housing;

a flow control unit disposed within said housing lumen to control fluid flow from the bladder;

a distal retainer attached to said housing distal region; and a proximal retainer attached to said housing proximal region, wherein said distal retainer is adapted to be slidably received within said housing lumen and biased to expand radially when pushed distally from said housing lumen.

2. A bladder control apparatus as recited in claim 1, wherein said housing includes an inner housing having a lumen therethrough and a distal region, having said distal retainer attached to said inner housing distal region and having said flow control unit within said inner housing lumen;

an outer housing having a lumen and a proximal region and distal region having said proximal retainer attached to said outer housing proximal region, and having said inner housing within said outer housing lumen.

3. A bladder control apparatus as recited in claim 2, wherein said outer housing distal region includes a soft elastic tip having a radially expandable lumen therethrough.

4. A bladder control apparatus as recited in claim 3, further comprising an insertion rod having a distal region, wherein said inner housing has a proximal region adapted to be releasably attached to the distal region of the insertion rod.

5. A bladder control apparatus as recited in claim 4, wherein said inner housing proximal region and said insertion rod distal region are threaded to releasably attach to each other.

6. A bladder control apparatus as recited in claim 2, wherein said distal retainer includes a plurality of arms biased to be radially disposed when unconstrained.

7. A bladder control apparatus as recited in claim 6, wherein said distal retainer arms are formed of polymeric material and are circumferentially interconnected.

8. A bladder control apparatus as recited in claim 2, wherein said outer housing has a proximal region adapted to be releasably attached to the distal end of a pusher assembly.

9. A method for inserting a female bladder control device within a urethra comprising the steps:

providing a bladder control device having a distal region and a proximal region including an outer housing having a lumen therethrough, a distal region, and a proximal retainer, an inner housing disposed within said outer housing lumen, having a lumen therethrough such that fluid from the bladder can flow through the inner housing, a proximal region, and an expandable distal retainer, said distal retainer slidably disposed within said outer housing, and a flow control unit disposed within said inner housing lumen to control fluid flow from the bladder;

inserting said bladder control device distally into said urethra; and applying force distally to said inner housing, causing said distal retainer to move distally past said outer housing distal region and into said bladder and expand to a radial extent greater than the radial extent of said urethra.

10. A method as recited in claim 9, further comprising providing an insertion rod having a distal region, wherein said force applying step includes pushing said insertion rod distal end against said inner housing.

11. A method as recited in claim 10, wherein said insertion rod distal region is adapted to releasably attach to said inner housing proximal region, further comprising attaching said insertion rod distal region to said inner housing proximal region prior to said force applying step and detaching said insertion rod distal region from said inner housing proximal region after said force applying step.

12. A method as recited in claim 10, further comprising:

providing a pusher assembly including a distal barrel having a lumen adapted to slidably contain said insertion rod, said pusher assembly including a proximal plunger adapted to slide within said barrel, and disposing said insertion rod within said barrel, wherein said force applying step further includes sliding said plunger distally within said barrel, causing said insertion rod to move distally.

\* \* \* \* \*